US00PP21356P3

(12) United States Plant Patent

Gmitter, Jr. et al.

(10) Patent No.: US PP21,356 P3

(45) Date of Patent: Oct. 5, 2010

(54) MANDARIN TREE NAMED 'LB8-9'

(50) Latin Name: ***Citrus reticulata*×(*Citrus paradisi*× *Citrus reticulata*)**

Varietal Denomination: LB8-9

(75) Inventors: Frederick G. Gmitter, Jr., Lakeland, FL (US); William S. Castle, Lake Alfred, FL (US); Jude W. Grosser, Winter Haven, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 18 days.

(21) Appl. No.: 12/313,081

(22) Filed: Nov. 17, 2008

(65) Prior Publication Data

US 2010/0125922 P1 May 20, 2010

(51) Int. Cl.

*A01H 5/00* (2006.01)

(52) U.S. Cl. ..... Plt./201

(58) Field of Classification Search ..... Plt./201, Plt./202

See application file for complete search history.

(56) References Cited

OTHER PUBLICATIONS

Dou et al.; Postharvest quality and acceptance of LB8-9 mandarin as a frest fruit cultivar; Horttechnology, 2007, vol. 17, No. 1 (Jan.-Mar.); Abstract.

*Primary Examiner*—Kent L Bell

(74) *Attorney, Agent, or Firm*—Jondle & Associates, P.C.

(57) ABSTRACT

A new Mandarin hybrid tree particularly distinguished by having dense foliage, "wilted-leaf" appearance, fruit that is attractive in appearance with excellent eating quality, and upright, vigorous plant habit, obloid tree shape and matures early in central Florida, is disclosed.

3 Drawing Sheets

Genus and species: *Citrus reticulata*×(*Citrus paradisi*× *Citrus reticulata*).

Variety denomination: 'LB8-9'.

BACKGROUND OF THE NEW PLANT

The invention relates to a new and distinct variety of mandarin *Citrus reticulata*×(*Citrus paradisi*×*Citrus reticulata*) hybrid tree named 'LB8-9'. 'LB8-9' is a vigorous tree that produces fruit similar in shape to a commonly grown tangelo 'Minneola' (unpatented), itself a hybrid of *C. paradisi*×*C. reticulata*. 'LB8-9' produces fruit that are very highly colored internally and externally, with excellent eating quality. 'LB8-9' ripens 4 to 6 weeks before 'Minneola' depending on season and rootstock, usually from late November to early January in central Florida. 'LB8-9' is also very tolerant of Alternaria brown spot, which is a pathogen that severely attacks foliage and fruit of 'Minneola' tangelo.

'LB8-9' mandarin hybrid originated from a cross made between 'Clementine' (unpatented) tangerine and 'Minneola' (unpatented) tangelo, during the 1970s in Lake Alfred, Fla. 'LB8-9' was among more than 120 hybrids derived from crosses on to 'Clementine' tangerine using a variety of pollen parents, that were propagated onto 'Cleopatra' mandarin (*Citrus reshni*) for use as breeding parents. 'LB8-9' first was selected in 1985 from among this collection of hybrids. After 3 years of observation, the tree was selected for further propagations and evaluation because of its similarity to 'Minneola' tangelo, that it matures 4 to 6 weeks earlier than 'Minneola', and has excellent eating quality. The asexual propagation method was conducted by budding onto several different rootstocks. Once the propagations were made, the plants were planted in a cultivated area in Lake Alfred, Fla. Asexually propagated trees of 'LB8-9' have remained true to the original selected budded tree selected, and all characteristics of the fruit and tree have been transmitted and retained through three successive asexual vegetative generations.

Plant Breeder's Rights for this cultivar have not been applied for. 'LB8-9' has not been made publicly available more than one year prior to the filing of this application.

SUMMARY OF THE INVENTION

The new and distinct variety of mandarin hybrid (tangerine) bears fruit that ripens from late November to mid January in central Florida. The trees usually bloom between early to late March in central Florida, depending on the season, and they grow vigorously. 'LB8-9' trees bear fruit that resembles the 'Minneola' tangelo in shape, tend to be a bit smaller (between 70 mm and 130 mm depending on tree crop load), with deeper orange-red color internally and externally, and with excellent eating quality. The fruit are juicy, but can be fairly easily peeled. They are very sweet, but usually with substantial acidity to balance the high level of sugars. They ripen 4 to 6 weeks earlier than 'Minneola' tangelo. Both color and flavor of 'LB8-9' fruit exceeds 'Minneola'. The fruit of 'LB8-9' may be seedy when cross-pollinated, but they can have substantially reduced seed numbers, even be seedless, when grown in solid blocks with minimal cross-pollination, or when treated with growth regulators such as gibberellic acid, to increase fruit set.

In addition, their high levels of tolerance to Alternaria brown spot, especially when compared to the very susceptible 'Minneola' tangelo, is an advantage to growers, consumers, and the environment since fungicide applications to control Alternaria may be reduced from 10 to 15 times per year on 'Minneola', to 2 to 5 applications for other fungal pathogens only. Young trees are very vigorous reaching 2 meters in height or more in two years, and they tend to be slow to come into bearing, usually flowering for the first time in their $4^{th}$ year; this can be altered by trunk girdling in the autumn with abundant flowers produced the following spring. After seasons with a heavy crop, it is common for there to be few or no fruit set the following year; this alternate bearing tendency may be on the whole tree basis though sometimes it can be seen to differ by limbs within the tree. The following are the most outstanding and distinguishing characteristics of this new cultivar when grown under normal horticultural practices in Florida.

1. Dense foliation;
2. Characteristic "wilted-leaf" appearance;
3. Bearing fruit that are attractive in appearance with excellent eating quality;
4. Upright and vigorous plant habit;
5. Obloid tree shape; and
6. Matures early in central Florida.

DESCRIPTION OF THE PHOTOGRAPHS

This new mandarin tree is illustrated by the accompanying photographs which show the tree's form, foliage and fruit. The colors shown are as true as can be reasonably obtained by conventional photographic procedures. The photographs are of a tree approximately 10-years old. FIG. 1 was taken in the spring-time, while FIGS. 2-6 were taken during the early winter from the same tree.

DESCRIPTION OF THE NEW CULTIVAR

Figure 1:
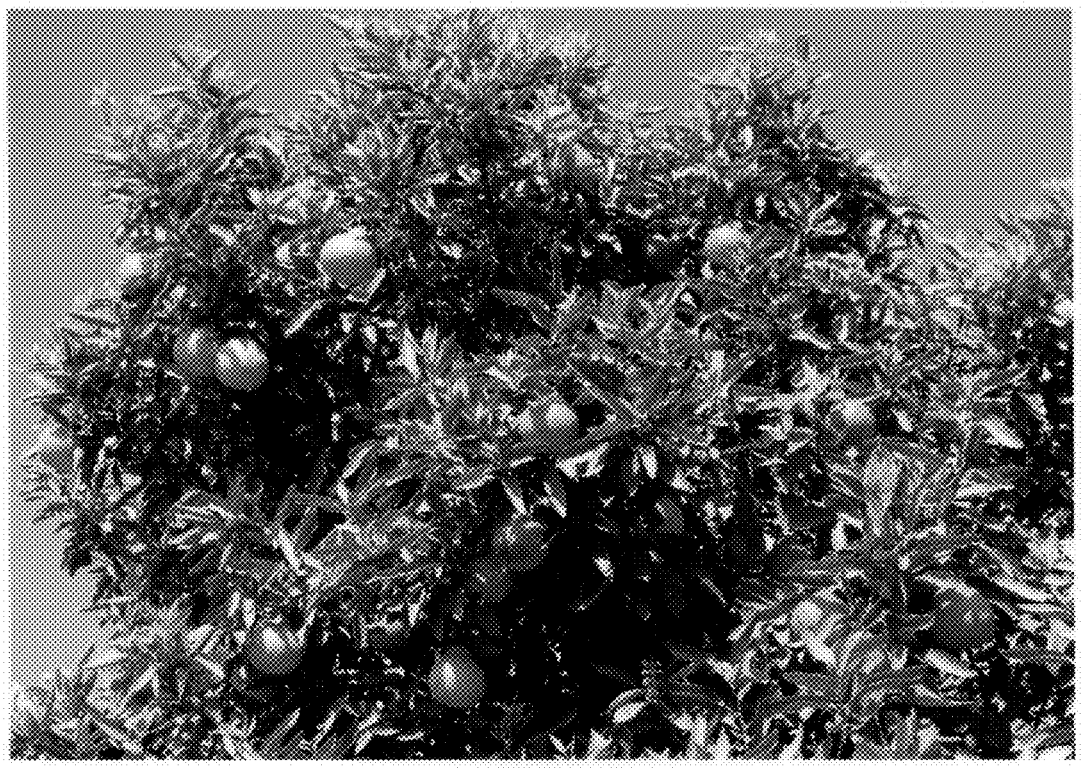
FIG. 1 shows the overall plant habit including foliage and fruit taken in the spring-time.
Figure 2:
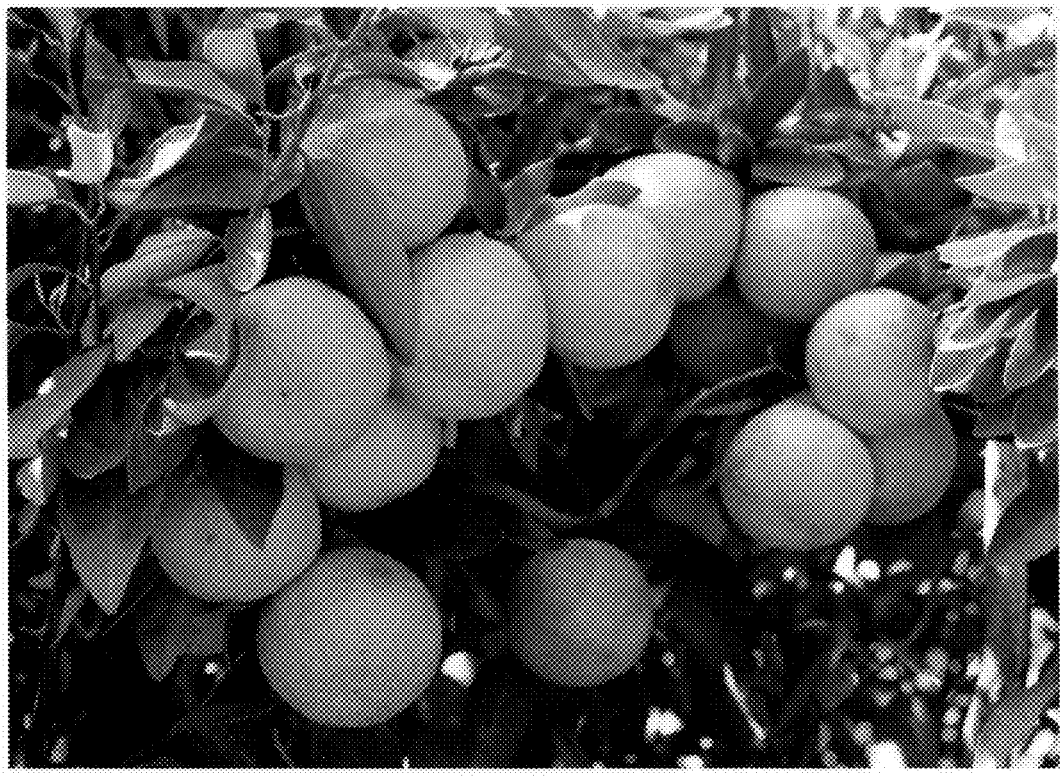
FIG. 2 shows mature fruit hanging on the tree.
Figure 3:
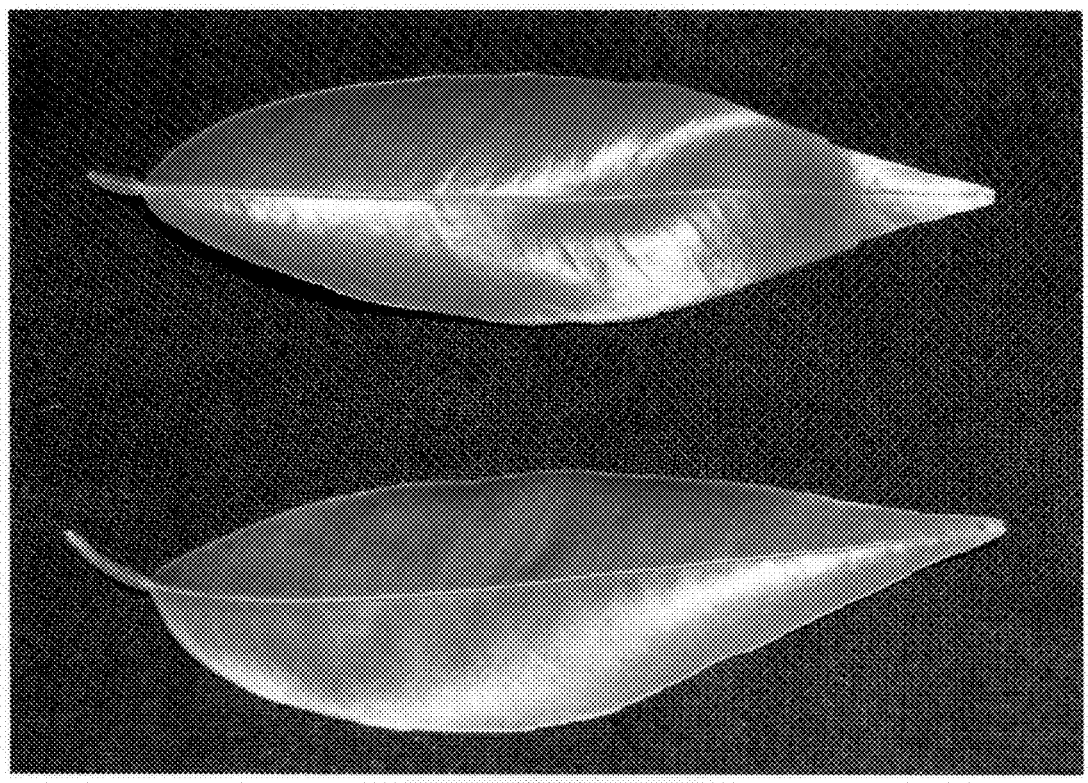
FIG. 3 shows a close-up of the mature leaves.
Figure 4:
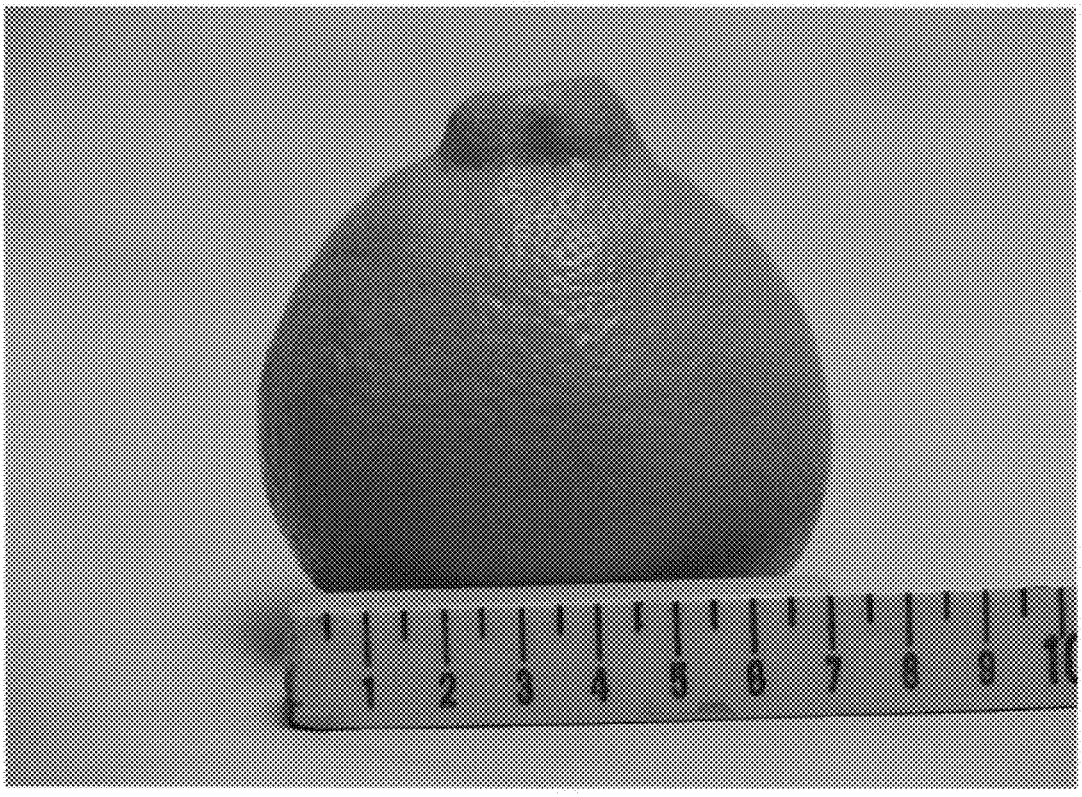
FIG. 4 shows a close-up of the mature fruit with the rind present.
Figure 5:
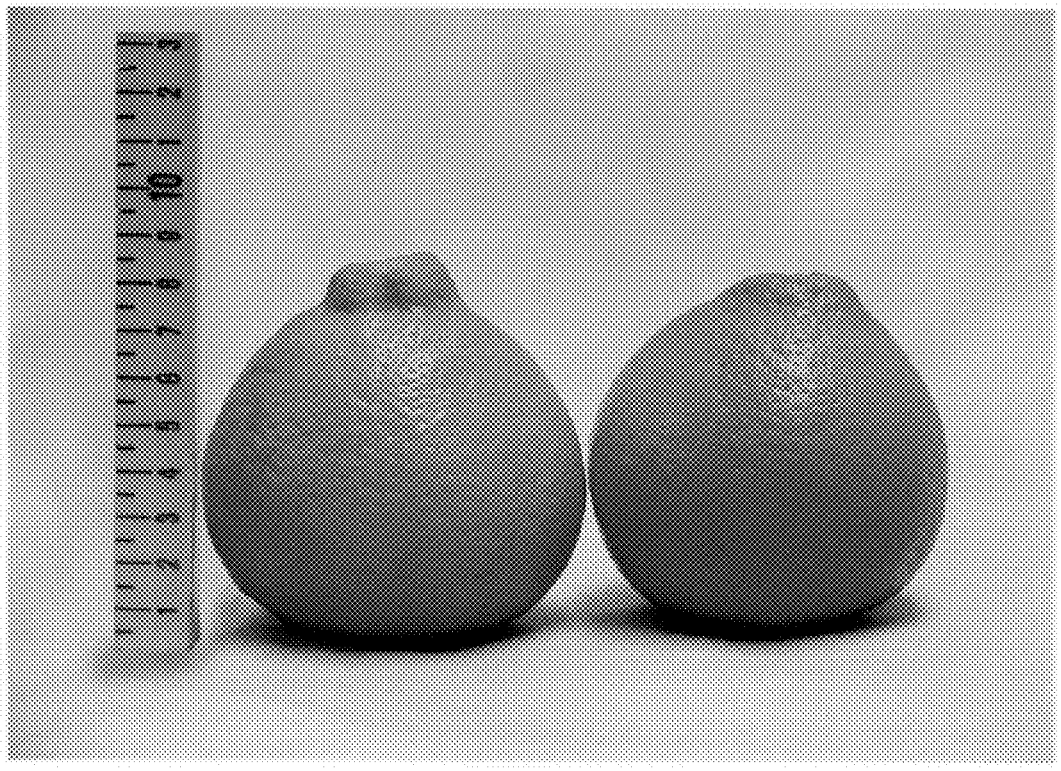
FIG. 5 shows an additional close-up of the mature fruit with the rind present.
Figure 6:
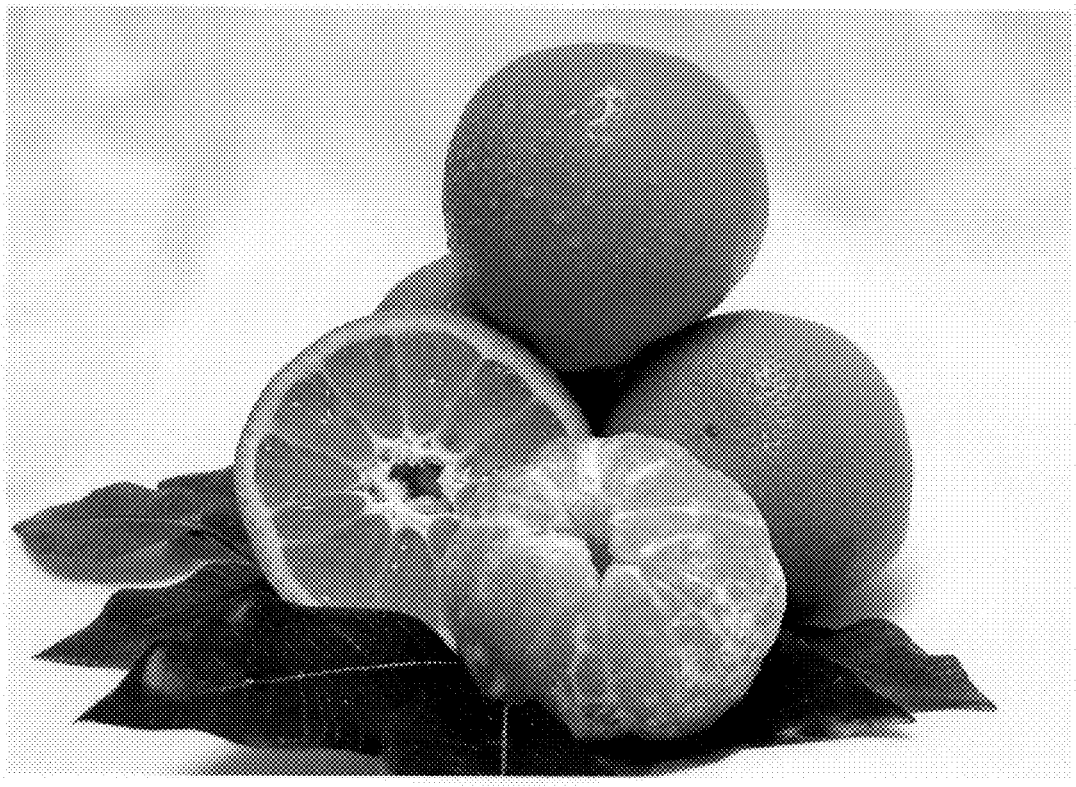
FIG. 6 shows a close-up of the mature fruit without the rind and a cross-sectional view of the fruit when cut in the center.

The following detailed description sets forth the distinctive characteristics of 'LB8-9'. The present botanical description is that of the variety grown on 10-year-old trees growing on Carrizo citrange rootstock (*C. sinensis*×*Poncirus trifoliata*) in Lake Alfred, Fla. The colors (except those in common terms) are described from R.H.S. Colour Chart published by The Royal Horticultural Society in London (second edition), in association with the Flower Council of Holland.

DETAILED BOTANICAL DESCRIPTION

Classification:

*Botanical.*—*Citrus reticulata*×(*Citrus paradisi*×*Citrus reticulata*).

*Common name.*—Mandarin hybrid or Tangerine.

Parentage:

*Female parent.*—'Clementine' (unpatented) tangerine.

*Male parent.*—'Minneola' (unpatented) tangelo.

Tree:

*Ploidy.*—Diploid.

*Size.*—Large, with heights of 3 m to 7 m if un-pruned.

*Vigor.*—Very vigorous, growing shoots of 1 m or more typically from strong spring flush on young trees.

*Density.*—Canopies are quite dense, because of vigor and because of leaf tolerance to Alternaria which greatly minimizes leaf loss.

*Diameter* (10 *year old tree, un-pruned*).—7 m.

*Form.*—The shape of the tree is obloid with upright branches prior to fruiting, but tending toward medium angles after fruit has commenced.

*Growth habit* (*current season*).—Drooping.

Trunk and branches:

*Trunk texture.*—Smooth.

*Trunk diameter* (6 *year old tree*).—16.9 cm at 30 cm above the ground.

*Trunk bark color.*—RHS 200A (brown); irregularly striated with RHS 144A and RHS 144B (yellow-green).

*Branch length* (*from the first crotch point to tip of leaf branch*).—3.65 m.

*Crotch angle.*—Varies from 30 to 60 degrees from the main trunk.

*Branch texture.*—Relatively smooth and without thorns or spines.

*Branch color* (*shoots from previous flush, hardened and* 4 *mm to* 5 *mm in diameter*).—RHS 146A (yellow-green).

Leaves:

*Size* (*lamina average*).—Length: 110 mm. Width: 40 mm. L/W ratio: 2.7 to 2.9.

*Thickness.*—Regular and average for commercial mandarin hybrids.

*Type.*—Simple.

*Shape.*—Elliptical.

*Apex.*—Retuse.

*Base.*—Acute to sub-obtuse.

*Margin.*—Entire, undulate.

*Surface.*—Upper surface: Glabrous. Lower surface: Medium veins that are pinnately netted.

*Color.*—Upper surface (adaxial): RHS 137A (green). Lower surface (abaxial): RHS 146A (yellow-green).

*Petiole.*—Shape: Brevipetiolate (shorter than leaf lamina); junction between petiole and lamina is articulate. Width (petiole wing): Very narrow. Shape (petiole wing): Obovate. Length: 15 mm. Width: 3 mm. Color: RHS 137A (green).

Flowers:

*Type.*—Hermaphrodite.

*Bud.*—Shape: Immature: Round dome. Mature: Elongated olive. Length: Immature: 2.0 mm. Mature (before fully open): 16.0 mm. Diameter: Immature: 2.2 mm. Mature (before fully open): 7.0 mm. Color (immature): RHS 144D (yellow-green).

*Petals.*—Number: 5. Color: Upper surface: RHS 155C (white) to RHS 155B (white). Lower surface: RHS 155C (white) with RHS 150D (yellow-green) spots distributed toward the petal apex. Length: 18 mm. Width: 5 mm. Shape: Flat, spatula-shaped. Apex: Smooth acute. Base: Even obtuse. Margin: Smooth.

*Sepals.*—Number (per flower): 6. Shape: Short flat delta with obtuse angle at apex. Length: 2.0 mm. Width: 2.0 mm. Apex: Round or obtuse angle at apex. Margin: Smooth. Color: Upper surface: RHS 144D (yellow-green). Lower surface: RHS 144D (yellow-green).

*Pedicel.*—Length: 4.5 mm to 6.6 mm. Diameter: 0.8 mm to 1.2 mm. Color: RHS 143B (green).

*Calyx.*—Small.

*Arrangement.*—Flowers grown from leaf axillaries in clust, each cluster consists of 2 to 6 flowers; flowers also borne singly on new leafy shoots, terminal and from sub-terminal nodes.

*Blossom period.*—First bloom: Around February 21$^{st}$ in Central Florida. Full bloom: Early April in Central Florida.

*Fragrance.*—Moderate compared with other citrus blossoms.

Reproductive organs:

*Fertility* (*determined by hand pollination tests*).—Self-fertile; however fruit sets are typically lower in solid planted blocks with minimal cross-pollination, indicating some degree of self-infertility.

*Stamen.—Number:* 4 per petal. Stamen length: 12.5 mm.

*Anther.*—Length: 3.4 mm. Width: 0.9 mm. to 1.0 mm.

*Color.*—RHS 13B (yellow).

*Anther filament length.*—Shorter relative to stigma.

*Pistil.*—Number: 1. Length: 10.5 mm. Color: RHS 13C (yellow).

*Style.*—Length: 7.6 mm to 8.0 mm. Diameter: 1.0 mm. Color: RHS 143C (green).

*Ovary.*—Shape: Oval. Diameter: 2.2 mm. Color: RHS 143C (green).

*Pollen amount.*—Abundant.

*Pollen color* (*general*).—Bright-yellow.

Fruit:

*Size.*—Uniform, 70 mm to 130 mm in diameter.

*Length.*—69 mm to 85 mm.

*Weight* (*per individual fruit*).—160.0 g to 180.0 g.

*Shape.*—Pyriform.

*Shape* (*cross-section*).—Round.

*Apex.*—Truncate.

*Apex cavity diameter.*—Not applicable.

*Base.*—Necked.

*Base cavity diameter.*—6 mm to 7 mm.

*Stem* (*first node connecting to fruit*).—Length: Not applicable. Diameter: 3.0 mm to 4.0 mm. Color: RHS 138A (green) with RHS 198D (greyed-green) strip.

*Date of first harvest* (*based on season and rootstock*).—Around November 20th.

*Date of last harvest* (*based on season and rootstock*).—Around January 20th.

Rind:

*Adherence.*—Albedo (mesocarp) to flesh (endocarp) is medium, compared to other commercial mandarin hybrid varieties, but less adherent than 'Minneola' tangelos at a comparable stage of maturity; adherence is slight at the base and increases toward the apex.

*Thickness.*—2.6 mm (medium compared to other commercial mandarin hybrid varieties).

*Texture.*—Pitted.

*Color.*—Flavedo (epicarp): Ranges from between RHS 25A (orange) to RHS 33A (orange-red). Albedo (mesocarp): RHS 20B (yellow-orange).

*Stylar end.*—Closed.

*Rind oil cell density.*—86 to 89 per $cm^2$.

Flesh:

*Number of segments.*—Average between 10 and 14 segments per fruit.

*Segment walls.*—Medium, but of sufficient strength to maintain integrity as separated.

*Juice.*—Abundant.

*Color.*—Uniformly RHS 28A (orange).

*Texture.*—Soft.

*Vesicle length.*—Average ranges from 12.3 mm to 13.0 mm.

*Vesicle diameter* (*thickness*).—Average ranges from 1.8 mm to 2.0 mm.

*Eating quality.*—Soluble solids (average): 14.2 Brix. Acidity (average): 1.12%. Vitamin C content: 42.43 mg/100 ml; consistently higher than 'Minneola' (unpatented) tangelo with 23.27 mg/100 ml and 'Sunburst' (unpatented) tangerine with 26.25 mg/100 ml. Sucrose content: 7.14 g/100 ml.

Seeds:

*Type.*—Monoembryonic, with zygotic embryos only, in contrast to 'Minneola' tangelo which is polyembryonic and contains primarily nucellar embryos.

*Number.*—Ranges from 0 to 32, depending on the degree of cross-pollination and use of gibberellic acid or other growth regulators.

*Shape.*—Clavate to semi-deltoid.

*Size.*—Length: 15.6 mm. Width: 5.4 mm.

*Seed coat color.*—Outer surface: RHS 11 D (yellow) and wrinkled. Inner surface: RHS 165C (greyed-orange).

*Cotyledon color.*—RHS 145D (yellow-green).

Resistance to diseases: 'LB8-9' has been observed for over 10 seasons and in various locations in Florida, and compared with 'Minneola' tangelo for the incidence and severity of Alternaria infection on foliage and fruit. 'LB8-9' has consistently been found to be very tolerant of Alternaria, with only occasional fruit or foliage lesions observed. In two pairs of adjacent trees, one each of 'Minneola' tangelo and 'LB8-9', it was obvious that Alternaria infections in most seasons resulted in substantial defoliation of the 'Minneola' tangelo, but none was observed on 'LB8-9'. Young and expanding leaves were collected from 'LB8-9' and 'Minneola' tangelo, placed in covered plastic containers, misted with a suspension of Alternaria spores and held at 27° C. Within 3 to 4 days, the 'Minneola' tangelo leaves were completely browned, but the 'LB8-9' leaves exhibited only pinprick-sized lesions, with the uninfected leaf tissue remaining green. These tests were repeated three times with identical results. Trees and fruit have been observed to be free of scab lesions (*Elsinoe fawcetti* Bitanc. and Jenk.), a fungal pathogen of citrus. No other disease resistance characterizations have been made.

COMPARISON WITH PARENTAL AND KNOWN CULTIVARS

'LB8-9' differs from the female mandarin parent 'Clementine' (unpatented) by having fruit that matures later, is larger, much deeper orange colored rind and flesh colors at maturity under growing conditions in Florida than 'Clementine'. In addition, 'LB8-9' has a higher sugar content and acid percentage and peels with more difficulty than 'Clementine'.

Comparisons were made with the commercial variety 'Sunburst' (unpatented) tangerine and the male parent 'Minneola' (unpatented) tangelo, two cultivars that overlap the early and late seasons of maturity for 'LB8-9'. 'LB8-9' and 'Sunburst' fruit stored two weeks at 22° C. developed similar decay percentages (36%), while 'Minneola' had 16% decay. There was no rind "pitting" (a physiological maldady) by cold storage at 22° C. in 'LB8-9' or 'Minneola', and 3% in 'Sunburst' tangerines. No differences were found in fruit color or post-harvest losses among the three cultivars stored at 4° C. after 6 weeks. Taste panels were conducted one week and 7 weeks after fruit were stored at 4° C. No difference was found in fruit acceptance one week after packing, while a better score of acceptance was recorded for 'LB8-9' after 7 weeks. Generally, 'LB8-9' was characterized having a rich flavor. 'LB8-9' fruit had higher Brix (14.2) and acid percent (1.12%) than 'Minneola' or 'Sunburst', with Brix and acid lower than 11.5 and 0.86%, respectively. Sucrose concentration was noticeably higher in 'LB8-9', 7.14 g/100 mL, than in 'Min neola' 5.27 g/100 mL or 'Sunburst' 6.10 g/100 mL. Vitamin C concentration was 42.43 mg/100 mL for 'LB8-9', considerably higher than 'Minneola' (23.27 mg/100 mL) or 'Sunburst' (26.25 mg/100 mL). No unusual post-harvest storage problems were noted in two years of testing.

I claim:

1. A new and distinct cultivar of Mandarin tree as shown and described herein.

* * * * *